United States Patent  
Kazui et al.

(10) Patent No.: US 6,756,590 B2
(45) Date of Patent: Jun. 29, 2004

(54) SHAPE MEASUREMENT METHOD AND APPARATUS (75) Inventors: Masato Kazui, Tokyo (JP); Mitsuji Ikeda, Tokyo (JP); Atsushi Takane, Ibaraki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/421,140

(22) Filed: Apr. 23, 2003

(65) Prior Publication Data

US 2003/0197873 A1 Oct. 23, 2003

(30) Foreign Application Priority Data

Apr. 23, 2002 (JP) ........................................ 2002-120357

(51) Int. Cl.[7] .......................................... G01N 23/203
(52) U.S. Cl. ..................................................... 250/310
(58) Field of Search ................................ 250/310, 399, 250/492.1, 492.2, 492.3, 559.2, 559.24; 356/601, 625

(56) References Cited

U.S. PATENT DOCUMENTS 4,670,652 A * 6/1987 Ichihashi et al. ............ 250/310
6,157,032 A * 12/2000 Into ............................ 250/310
2003/0015660 A1 * 1/2003 Shishido et al. ............ 250/311

FOREIGN PATENT DOCUMENTS

| JP | 2-247964 | * 10/1990 | ........... G01B/15/04 |
|---|---|---|---|
| JP | 5-290786 | * 5/1993 | ........... H01J/37/28 |
| JP | 7-27549 | * 1/1995 | ........... G01B/15/00 |
| JP | 63-32314 | * 12/1998 | ........... G01B/15/00 |

* cited by examiner

*Primary Examiner*—John R. Lee
*Assistant Examiner*—Christopher M. Kalivoda
(74) *Attorney, Agent, or Firm*—Hogan & Hartson LLP (57) ABSTRACT An electron beam applied from an electron gun 1 and reflected off a surface of a specimen 7 placed on a stage 2 that is tilted at a tilt angle $\phi=0$ is detected, and a signal intensity thereof is measured by an electron detector 3. Based upon the measurement, an image processing unit 6 calculates a slope angle $\theta$ of the surface of the specimen, and determines candidates for cross-sectional shape of the specimen. Signal intensity of the electromagnetic wave that would be reflected from a surface having a cross-sectional shape of each of the candidates if the tilt angle $\phi$ were changed into $\phi=\phi_0$ are estimated, and compared with a signal intensity actually measured by the electron detector 3 with the tilt angle 100 being changed into $\phi=\phi_0$. Consequently, cross sectional shape and three-dimensional shape can be determined based upon a result of comparison, without utilizing a matching process of feature points.

13 Claims, 6 Drawing Sheets

SHAPE MEASUREMENT METHOD AND APPARATUS

BACKGROUND OF THE INVENTION

This invention relates to methods and apparatuses for measuring a shape, and particularly to a shape measurement method and apparatus suitable for measuring a cross-sectional or three-dimensional shape of a specimen in a nondestructive and contactless manner, utilizing a signal that is generated from the specimen upon exposure to electromagnetic waves (rays) or charged particle beams.

In order to form a wiring pattern on a semiconductor wafer, a coating called resist is applied to the semiconductor wafer; a mask on which the wiring pattern is formed is then placed over the resist, and visible rays or ultraviolet rays are applied through the mask to expose the resist and transfer the wiring pattern thereto. Thus-formed wiring pattern has sloped portions liable to change in slope angle and/or in shape according to focus and exposure dose of visible or ultraviolet rays that are applied, and thus requires measuring and testing in three-dimensional shape of the pattern to form a high-precision wiring pattern. For the purpose of testing the pattern, a wafer could be cut to precisely measure a cross section thereof, which would however require extra processes and costs.

In view of these circumstances, methods for measuring a cross-sectional shape of a pattern in a nondestructive and contactless manner utilizing an electron microscope image have been proposed. For example, JP 61-290313 A (also published under JP 5-54605 B2, and corresponding to Japanese Patent No. 1,842,661) has proposed measurement of a cross-sectional shape performed by a combined use of the "Shape from shading" (as disclosed in Ikeuchi, et al., "Determining 3D Shape from 2D Shading Information Based on the Reflectance Map Technique", IEICE Transactions, Vol. J-65-D, No. 7, pp.842–849, issued by The Institute of Electronics, Information and Communication Engineers, in July, 1982) method and the stereo matching method. The methodology disclosed in JP 61-290313 includes detecting feature points of a signal waveform detected by a secondary electron detector provided in an electron microscope, measuring an absolute value of a height of the cross section by stereo matching of the feature points, thereby obtaining a shape between the feature points by the "Shape from shading" method.

The Spectroscopic Critical Dimension Metrology as disclosed in J. A. Allgair, et al., "Implementation of spectroscopic critical dimension (SCD) for gate CD control and stepper characterization", SPIE proceedings, Vol. 4344, paper 57, 26$^{th}$ Annual International Symposium on Microlithography, issued by The International Society for Optical Engineering, in February 2001; is also known in the art. In this method, in order to prevent damage to a resist pattern that would be caused by irradiation with ultraviolet rays, a visible ray is applied to a specimen, and a reflected light spectrum from the specimen is compared with those corresponding to various three-dimensional shapes which have been stored in a database in advance, so that the three-dimensional shape of the specimen is extrapolated.

Other disclosures related to the above techniques may also be found for example in JP 7-27549 A, JP 2-247964 A (corresponding to Japanese Patent No. 2,716,997), JP 5-290786 A, JP 63-32314 A (also published under JP 7-122574 B2), and JP 1-143127 A (corresponding to Japanese Patent No. 2,650,281).

The use of the stereo matching method as described above would disadvantageously cause misalignment between corresponding feature points due to a low signal-to-noise ratio of an input signal, producing an appreciable error in measuring a three-dimensional shape. On the other hand, the SCD Metrology as described above requires data obtained by measurement to construct a database, and has a limitation placed on measurable patterns; i.e., line repetition structures/lattice patterns only can be measured by this method. In addition, outputs are not provided with stereoscopic representation, but in the form of numerical data (width and height of wiring, and slope angles), which would not be adequate to show a three-dimensional shape.

Furthermore, the existing techniques as above give no adequate consideration to measuring three-dimensional shapes of varied patterns using a single secondary electron detector.

SUMMARY OF THE INVENTION

The present invention is made in view of the aforementioned disadvantages, and it is an exemplified general object of the present invention to provide a shape measurement method and apparatus that can precisely measure a cross-sectional or three-dimensional shape of a specimen, without utilizing a matching process of feature points.

The present invention adopts the "Shape from shading" method to pick up more than one of candidates for cross-sectional shape or three-dimensional shape of a specimen, from which an appropriate shape conformable to an actual measurement result is selected as a measurement of the cross-sectional shape or three-dimensional shape of the specimen.

To be more specific, a shape measurement method according to one exemplified aspect of the present invention includes the steps of: applying one of an electromagnetic wave and a beam of charged particles to a surface of a specimen, using an irradiation unit that moves along an axis parallel to a scanning direction relative to the surface of the specimen; measuring a signal intensity of one of an electromagnetic wave reflected from the surface of the specimen and a beam of charged particles generated from the surface of the specimen as a result of irradiation from the irradiation unit; calculating a slope angle of the surface of the specimen at a position irradiated with one of the electromagnetic wave and the beam of charged particles on the basis of the measured signal intensity; determining candidates for cross-sectional shape of the specimen on the basis of the calculated slope angle; estimating a signal intensity of one of an electromagnetic wave that would be reflected from a surface having a cross-sectional shape of each of the candidates and a beam of charged particles that would be generated from the surface having a cross-sectional shape of each of the candidates if an angle of incidence of one of the electromagnetic wave and the beam of charged particles with respect to the surface having a cross-sectional shape of each of the candidates were changed to a specific angle of incidence different from an angle of incidence of one of the electromagnetic wave and the beam of charged particles applied to the surface of the specimen; comparing the estimated signal intensity with a signal intensity obtained by measurement performed when the angle of incidence of one of the electromagnetic wave and the beam of charged particles applied to the surface of the specimen is changed to the specific angle of incidence; and determining the cross-sectional shape of the specimen on the basis of a result of the comparing step.

In the shape measurement method as above, the irradiation unit may be designed to further move along an axis perpendicular to the scanning direction relative to the surface of the specimen, so that the irradiation unit applies one of an electromagnetic wave and a beam of charged particles to the surface of the specimen while moving relative to the specimen along the axis parallel to the scanning direction (x-axis) and along the axis perpendicular to the scanning direction or parallel to the longitudinal direction (y-axis). Moreover, when the cross-sectional shape (variations in thickness) of the specimen is determined on the basis of the result of tile comparing step, the determined cross-sectional shape is accumulated each time when the irradiation unit moves along the axis perpendicular to the scanning direction, so that a three-dimensional shape of the specimen may be determined on the basis of a result of the accumulating step.

In the above shape measurement method, preferable features include:

(1) prior to determining candidates for cross-sectional shape, the slope angle of the surface of the specimen at a position irradiated with one of the electromagnetic wave and the beam of charged particles may be calculated using the measured signal intensity and multiple parameters selected from various kinds of parameters relating to the cross-sectional shape of the specimen;

(2) in order to accurately determine the cross-sectional shape of the specimen, the multiple parameters to be used may be selected among those serving to reduce a difference between the measured signal intensity and the estimated signal intensity;

(3) in order to accurately determine the cross-sectional shape of the specimen, more preferably, the multiple parameters may be repeatedly selected until the difference between the measured signal intensity and the estimated signal intensity is reduced to a minimum;

(4) the candidates for cross-sectional shape that have been determined, the cross-sectional shape that has been determined, and the multiple parameters that have been selected may be stored in a database; and (5) when the angle of incidence of one of the electromagnetic wave and the beam of charged particles applied to the surface of the specimen is changed to the specific angle of incidence, an angle of placement of the specimen may be changed while an angle of irradiation of the irradiation unit is fixed at a predetermined angle; or, to the contrary, an angle of irradiation of the irradiation unit may be changed while the angle of placement of the specimen is fixed at a predetermined angle.

According to the method as described above, a slope angle of the surface of the specimen is calculated from a signal intensity that is obtained by actually applying an electromagnetic wave or a beam of charged particles to the specimen. Based upon the calculated slope angle, more than one candidate for cross-sectional shape of the specimen is for example determined. Assuming that the electromagnetic wave or the beam of charged particles were applied to the surface having a cross-sectional shape of each of the candidates with an angle of incidence being changed to a specific angle of incidence different from that of the electromagnetic wave or the beam of charged particles actually applied to the surface of the specimen, a signal intensity that would be obtained from each of the candidates for cross-sectional shape of the specimen is estimated. The estimated signal intensity is then compared with a signal intensity obtained by measurement performed when the angle of incidence of one of the electromagnetic wave and the beam of charged particles applied to the surface of the specimen is changed to the specific angle of incidence. Based upon a result of the comparison, the cross-sectional shape of the specimen is determined by selecting a cross-sectional shape serving to reduce a difference between the measured signal intensity and the estimated signal intensity as a most probable cross-sectional shape of the specimen. Therefore, the cross-sectional shape of the specimen can be acquired using an absolute value of the height (or thickness; i.e., distance measured along z-axis) of the specimen, without using a matching process of feature points. Further, accumulation of cross-sectional shapes of the specimen obtained while the irradiation unit moves in the scanning direction, which is performed each time when the irradiation unit moves along the axis perpendicular to the scanning direction (or along the longitudinal direction; i.e., along y-axis) enables determination of a three-dimensionial shape of the specimen.

A shape measurement apparatus according to another exemplified aspect of the present invention includes: an irradiation unit that applies one of an electromagnetic wave and a beam of charged particles to a surface of a specimen, while moving along an axis parallel to a scanning direction relative to the surface of the specimen; a signal intensity measurement unit that measures a signal intensity of one of the electromagnetic wave reflected from the surface of the specimen and the beam of charged particles generated from the surface of the specimen as a result of irradiation from the irradiation unit; a cross-sectional shape candidate determination unit that calculates a slope angle of the surface of the specimen at a position irradiated with one of the electromagnetic wave and the beam of charged particles on the basis of the signal intensity measured in the signal intensity measurement unit, and determines candidates for cross-sectional shape of the specimen on the basis of the calculated slope angle; a signal intensity estimation unit that estimates a signal intensity of one of an electromagnetic wave that would be reflected from a surface having a cross-sectional shape of each of the candidates and a beam of charged particles that would be generated from the surface having a cross-sectional shape of each of the candidates if an angle of incidence of one of the electromagnetic wave and the beam of charged particles with respect to the surface having a cross-sectional shape of each of the candidates were changed to a specific angle of incidence different from an angle of incidence of one of the electromagnetic wave and the beam of charged particles applied to the surface of the specimen; and a cross-sectional shape determination unit that compares the signal intensity estimated in the signal intensity estimation unit with a signal intensity obtained by measurement performed in the signal intensity measurement unit when the angle of incidence of one of the electromagnetic wave and the beam of charged particles applied to the surface of the specimen is changed to the specific angle of incidence, and determines the cross-sectional shape of the specimen on the basis of a result of the comparison.

In the shape measurement apparatus as above, the irradiation unit may be designed to further move along an axis perpendicular to the scanning direction relative to the surface of the specimen, so that the irradiation unit applies one of an electromagnetic wave and a beam of charged particles to the surface of the specimen while moving relative to the specimen along the axis parallel to the scanning direction (x-axis) and along the axis perpendicular to the scanning direction or parallel to the longitudinal direction (y-axis). The cross sectional shape is determined as described above while the irradiation unit moves along the axis parallel to the scanning direction, and the cross-sectional shape determination unit can accumulate thus-determined cross sectional shape each time when the irradiation unit moves along the axis perpendicular to the scanning direction, so that a three-dimensional shape of the specimen may be determined on the basis of a result of the accumulated cross-sectional shapes.

In the above shape measurement apparatus, preferable features include:

(1) the cross-sectional shape candidate determination unit may use the signal intensity measured in the signal intensity measurement unit and multiple parameters selected from various kinds of parameters relating to the cross-sectional shape of the specimen to calculate the slope angle of the surface of the specimen at a position irradiated with one of the electromagnetic wave and the beam of charged particles;

(2) the cross-sectional shape determination unit may instruct the cross-sectional shape candidate determination unit to select the multiple parameters among those serving to reduce a difference between the signal intensity measured in the signal intensity measurement unit and the signal intensity estimated in the signal intensity estimation unit;

(3) the cross-sectional shape determination unit may instruct the cross-sectional shape candidate determination unit to repeatedly select the multiple parameters until a difference between the signal intensity measured in the signal intensity measurement unit and the signal intensity estimated in the signal intensity estimation unit is reduced to a minimum; and (4) the candidates for cross-sectional shape that have been determined in the cross-sectional shape candidate determination unit, the cross-sectional shape that has been determined in the cross-sectional shape determination unit, and the multiple parameters that have been selected in the cross-sectional shape candidate determination unit may be stored in a database.

According to the apparatus as described above, a slope angle of the surface of the specimen is calculated from a signal intensity that is obtained by actually applying an electromagnetic wave or a beam of charged particles to the specimen. Based upon the calculated slope angle, more than one candidate for cross-sectional shape of the specimen is for example determined. Assuming that the electromagnetic wave or the beam of charged particles were applied to the surface having a cross-sectional shape of each of the candidates with an angle of incidence being changed to a specific angle of incidence different from that of the electromagnetic wave or the beam of charged particles actually applied to the surface of the specimen, a signal intensity that would be obtained from the candidates for cross-sectional shape of the specimen is estimated. The estimated signal intensity is then compared with a signal intensity obtained by measurement performed when the angle of incidence of one of the electromagnetic wave and the beam of charged particles applied to the surface of the specimen is changed to the specific angle of incidence. Based upon a result of the comparison, the cross-sectional shape of the specimen is determined by selecting a cross-sectional shape serving to reduce a difference between the measured signal intensity and the estimated signal intensity as a most probable cross-sectional shape of the specimen. Therefore, the cross-sectional shape of the specimen can be acquired using an absolute value of the height (or thickness; i.e., distance measured along z-axis) of the specimen by making use of a single unit for measuring signal intensity (signal intensity measurement unit), without using a matching process of feature points. Further, accumulation of cross-sectional shapes of the specimen obtained while the irradiation unit moves in the scanning direction, which is performed each time when the irradiation unit moves along the axis perpendicular to the scanning direction (or along the longitudinal direction; i.e., along y-axis) enables determination of a three-dimensional shape of the specimen.

Other objects and further features of the present invention will become readily apparent from the following description of preferred embodiments with reference to accompanying drawings.

DETAILED DESCRIPTION OF THE PREFERRED EMBODIMENTS

Figure 1:
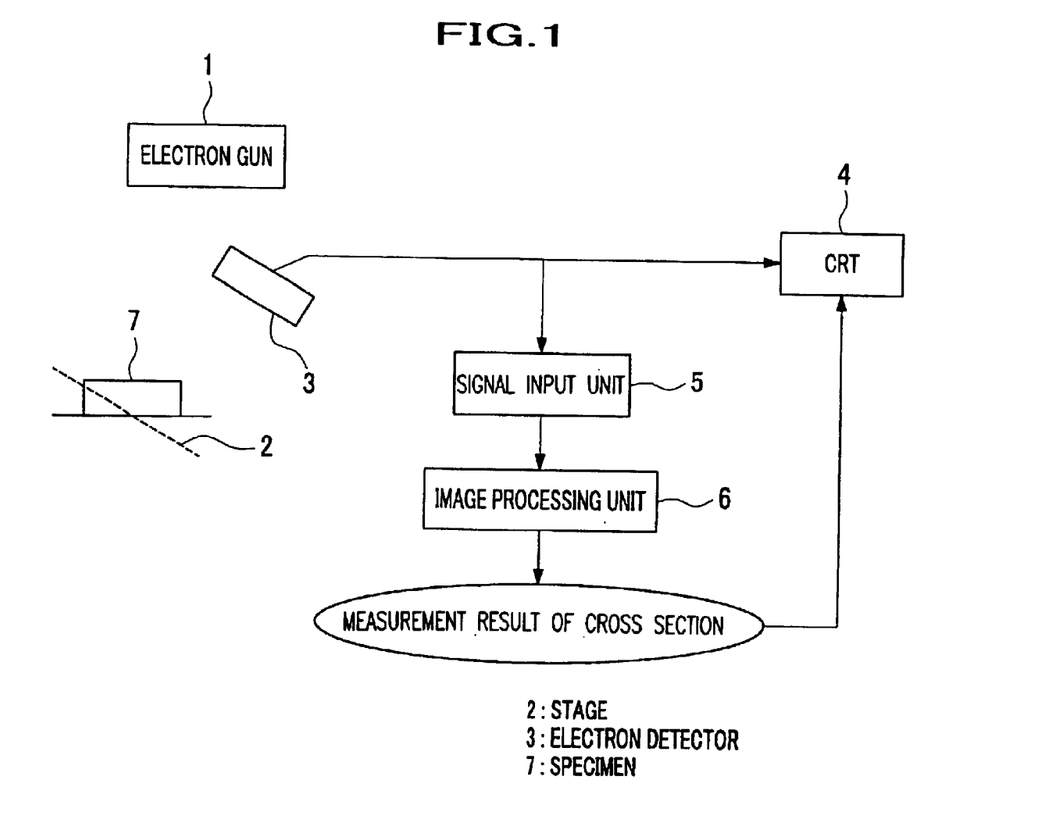
FIG. 1 is a block diagram showing a general arrangement of a three-dimensional shape measurement apparatus as one exemplified embodiment of the present invention.

One exemplified embodiment of the present invention will now be described with reference to the drawings. Referring to FIG. 1, which is a block diagram showing a general arrangement of a three-dimensional shape measurement apparatus as one exemplified embodiment of the present invention, the three-dimensional shape measurement apparatus includes an electron gun 1, a stage 2, an electron detector 3, a display unit (cathode ray tube or CRT) 4, a signal input unit 5, and an image processing unit 6. On the stage 2 is fixed a specimen 7.

The stage 2 is tiltable; in the present embodiment, the stage 2 may have a tilt angle selected from between $\phi=0$ and $\phi=\phi_0$. That is, an angle of placement of the specimen 7 fixed on the stage 2 is selectable from the tilt angles, i.e., between $\phi=0$ and $\phi=\phi_0$.

To the specimen 7 fixed on the stage 2, an electron beam of charged particles is emitted from the electron gun 1. In operation, the electron gun 1 applies an electron beam to the specimen 7 while moving along an axis parallel to a scanning direction (x-axis) relative to the specimen 7, and also applies an electron beam to the specimen 7 while moving along an axis perpendicular to the scanning direction (along a longitudinal axis or y-axis). When the electron beam is applied to the specimen 7, the electron beam that strikes on the specimen 7 serves as primary electrons to bombard a surface thereof, and thus causes secondary emission of part of the primary electrons, generating secondary electrons from the specimen 7. The secondary electrons, as thus generated, are detected by the electron detector 3. In other words, when an electron beam is applied from the electron gun 1 as an irradiation unit to the specimen 7, secondary electrons are generated from the specimen 7, and the secondary electrons are detected and signal intensity thereof is measured by the electron detector 5. The electron detector 3 serves as a signal intensity measurement unit that measures a signal intensity of the secondary electrons generated from the specimen 7. The signal intensity as measured in the electron detector 3 is output to the display unit 4 and the signal input unit 5. The signal input unit 5 is for example composed of an analog-to-digital converter, or the like. The signal input unit 5 receives a signal relating to the signal intensity measured in the electron detector 3, and outputs the same to the image processing unit 6 as a digital signal. The image processing unit 6 manipulates the signal, and outputs a manipulated result to the display unit 4, which in turn provides an on-screen representation of a cross-sectional shape measurement result.

The image processing unit 6 serves as a cross-sectional shape candidate determination unit to calculate a slope angle (angle formed between an incident beam and a reflected beam) of a surface of the specimen 7 at a position of incidence of the electron beam on the basis of the signal intensity measured in the electron detector 3, and to determine a cross-sectional shape (indicated by height or distance measured along z-axis of the specimen) of the specimen 7 from the calculated slope angle. The image processing unit 6 also serves as a signal intensity estimation unit to estimate a signal intensity of the electron beam that would be generated from a surface having a cross-sectional shape of each of the candidates if the electron beam were applied to the surface with an angle of incidence (angle of incidence when the tilt angle φ=0) of the electron beam with respect to the surface having a cross-sectional shape of each of the candidates being changed to a tilt angle φ=φ$_0$. The image processing unit 6 further serves as a cross-sectional shape determination unit to compare the signal intensity estimated in the signal intensity estimation unit with a signal intensity obtained by measurement performed in the electron detector 3 when the angle of incidence of the electron beam applied to the surface of the specimen 7 is changed, more specifically, when the tilt angle is changed from φ=0 to φ=φ$_0$, thereby determining the cross-sectional shape of the specimen 7. Moreover, the cross-sectional shape determination unit serves to accumulate the cross-sectional shape obtained while the electron gun 1 moves along the axis parallel to the scanning direction, each time when the electron gun 1 moves along the axis perpendicular to the scanning direction (along y-axis extending in the longitudinal direction), so that a three-dimensional shape of the specimen 7 may be determined on the basis of a result of the accumulated cross-sectional shapes.

Figure 2:
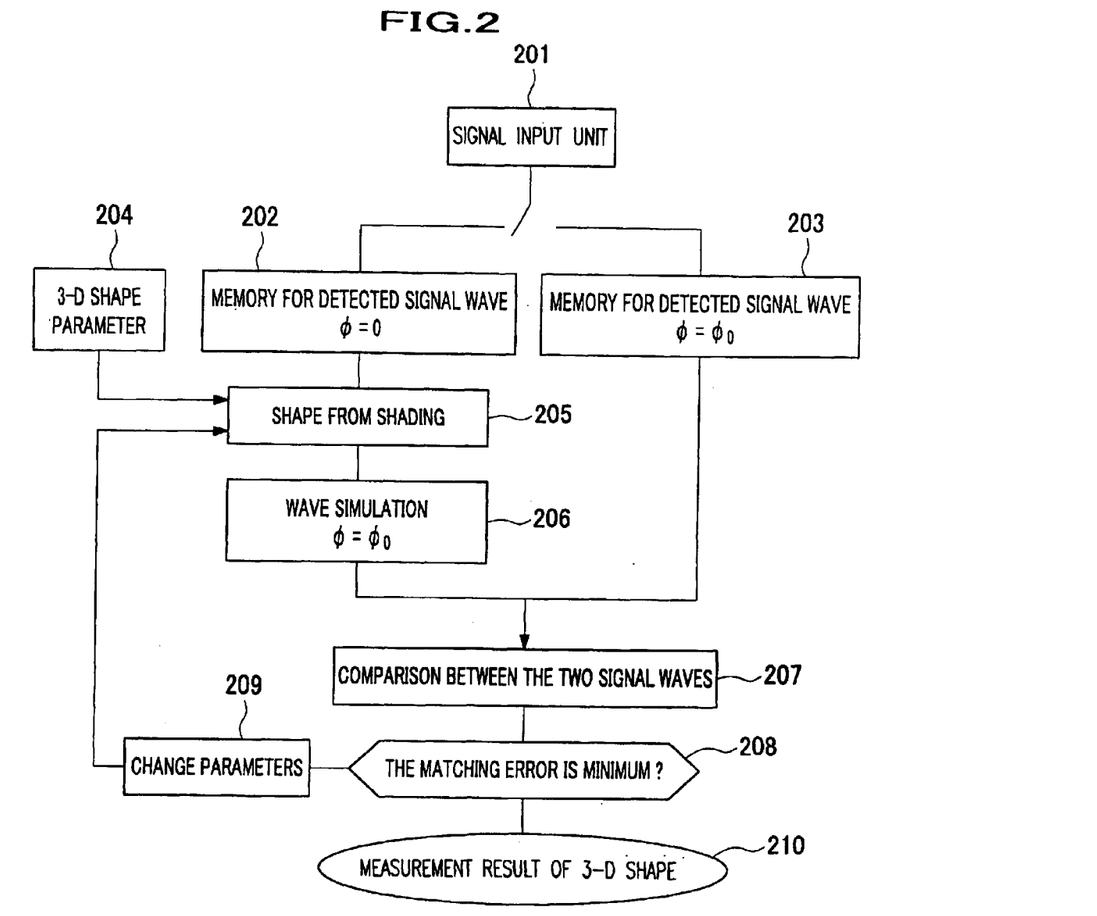
FIG. 2 is a flowchart for explaining process steps in an image processing unit.

To be more specific, as shown in FIG. 2, the image processing unit 6 acquires in sequence signals relating to signal intensities detected and measured by the electron detector 3 (step 201) while the electron gun 1 is applying an electron beam to the specimen 7. The image processing unit 6 then stores a signal intensity measured when the tilt angle φ of the stage 2 is φ=0 in a memory (step 202), and stores a signal intensity measured when the tilt angle φ of the stage 2 is changed to φ=φ$_0$ in a memory (step 203).

Based upon the signal intensity obtained when the tilt angle φ of the stage 2 is φ=0, the cross-sectional shape of the specimen 7 is calculated according to the "Shape from shading" method (step 205). At this stage, three-dimensional shape parameters such as a parameter n dependent on the quality of material of the specimen 7, and a parameter k relating to the height of the cross section of the specimen 7 are obtained (step 204), and a signal intensity I$_S$ of the secondary electrons is calculated by Equation (1) as shown below.

Hereupon, it is understood that the present embodiment makes use of a feature of the "Shape from shading" method in which secondary electrons reflected from the specimen 7 depends upon a slope angle (θ) of a cross section of the specimen 7.

Figure 3:
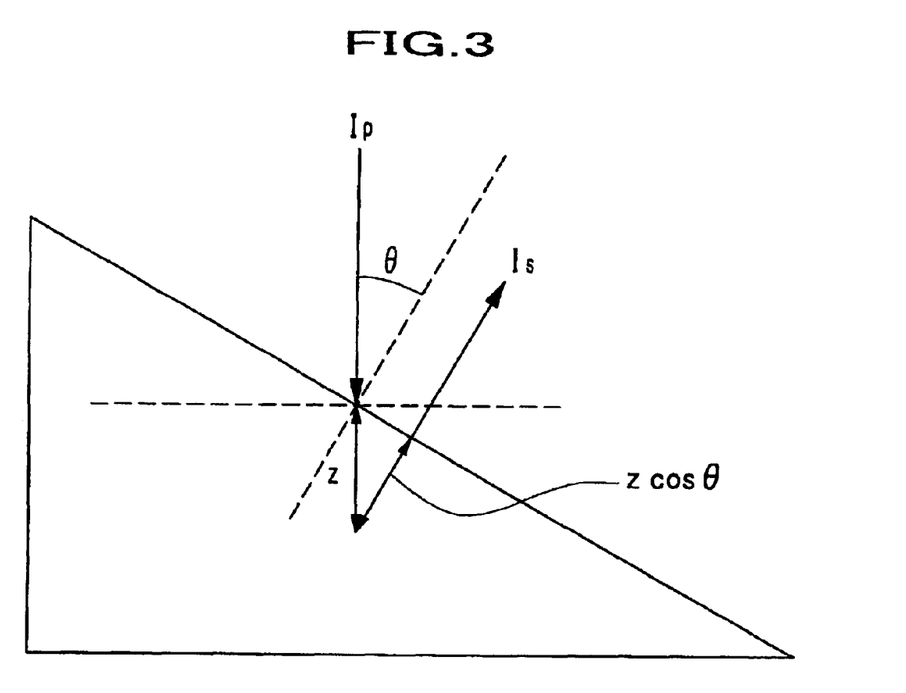
FIG. 3 is diagram for explaining dependency of intensity of a secondary electron on a slope angle of a surface of a specimen.

To be more specific, as shown in FIG. 3, when an electron beam is applied as primary electrons to a surface of the specimen 7, secondary electrons are generated in the specimen 7. The secondary electrons decrease exponentially in number within the specimen, but some reach the surface of the specimen 7, and are emitted out from the specimen 7. Accordingly, as described for example in "Sousa Denshi Kenbikyo (Scanning Electron Microscope)" edited by Kanto Affiliate, the Japanese Society of Microscopy (former Japanese Society of Electron Microscopy), published by Kyoritsu Shuppan Co., Ltd., 2000, the shorter the minimum escape distance zcos θ, the more the emission dose of the secondary electrons becomes; this relation is expressed by Equation (1) below. Denoted herein by I$_P$ is the signal intensity of a primary electron incident on the specimen 7, denoted by I$_S$ is the signal intensity of a secondary electron that is excited at a depth z in the specimen and reaches the surface of the specimen 7, and denoted by θ is an angle formed between an incident electron beam and a reflected electron beam.

$$I_S(x) = kI_o \sec^n \theta(x) \tag{1}$$

where I$_o$ is a signal intensity of a secondary electron in a flat region of the specimen 7, and x is a distance from the origin (rotation center) on one of the axes of coordinate (x-axis, i.e., axis parallel to the scanning direction). It is shown in Equation (1) that I$_S$(x) increases more as the slope angle θ becomes greater.

Figure 4A:
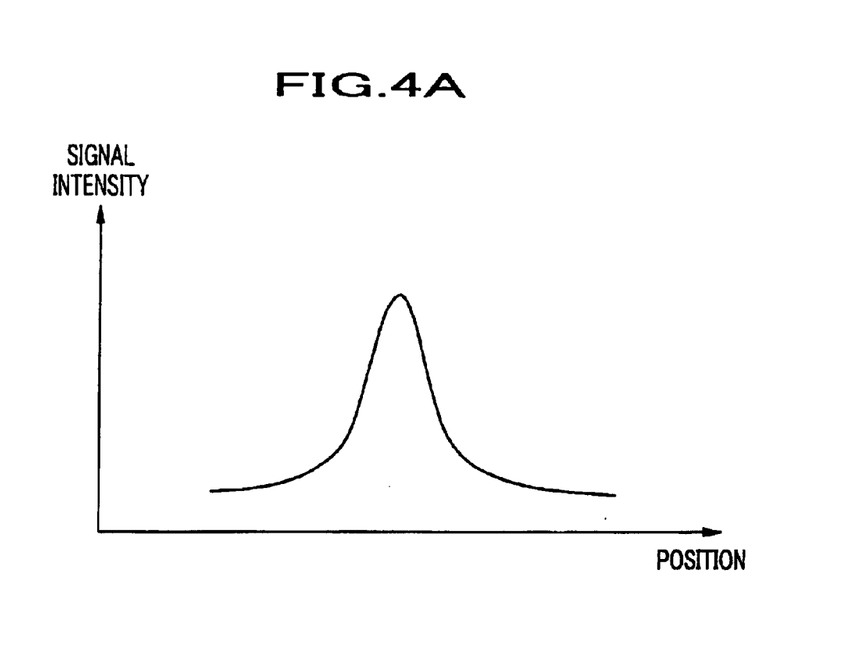
FIG. 4A is a graph showing a signal waveform of intensity of a secondary electron.

When a signal intensity of secondary electrons is measured in the electron detector 3 while an electron beam emitted from the electron gun 1 is scanning the surface of the specimen 1 in sequence, a signal waveform as shown in FIG. 4A is obtained to indicate a signal intensity measured at each scanned position.

When the waveform, as shown in FIG. 4A, relating to a signal intensity of the secondary electrons is obtained, the slope angle θ(x) of the cross section of the specimen 7 at a position x in the scanning direction is obtained from Equation (1) as expressed by Equation (2) below.

$$\theta(x) = \cos^{-1}\left(\frac{kI_o}{I_s(x)}\right)^{\frac{1}{n}} \tag{2}$$

Assuming that the height of the cross section of the specimen increases monotonously, a cross section profile h(x) of the specimen 7 is expressed by Equation (3) below.

$$h(x) = \int_0^x \tan\theta(\xi)d\xi \tag{3}$$

Figure 4B:
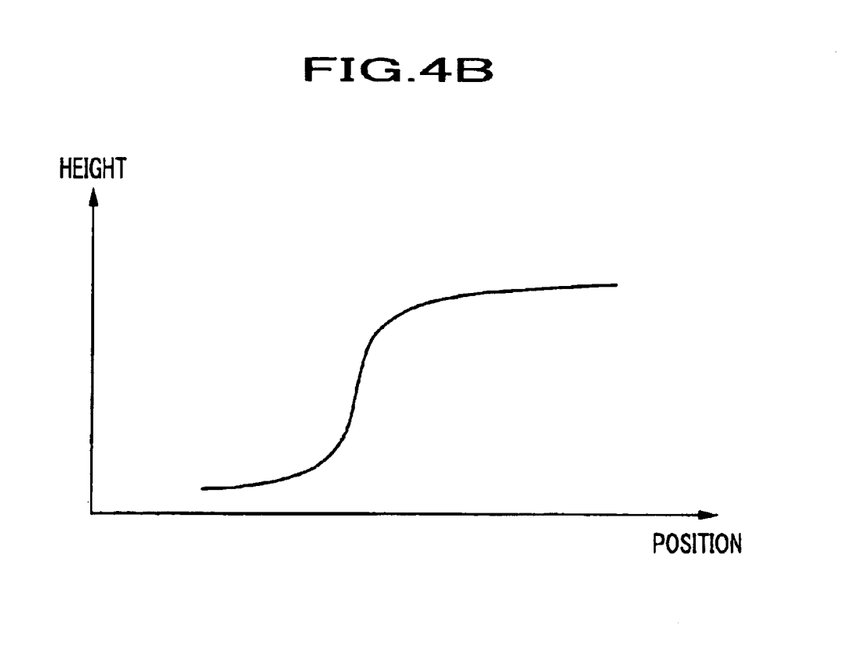
FIG. 4B is a graph showing a cross-sectional shape of a specimen as illustrated by plotting height (thickness) of the specimen with respect to scanned positions.

Thus, substitution of Equation (2) into Equation (3) yields the cross-sectional shape h(x). In this operation, a greater value of the slope angle θ implies a greater value of h(x). If a signal waveform as shown in FIG. 4A is obtained, a cross-sectional shape of the specimen 7 determined by a height (distance along z-axis) for each position x is obtained as shown in the graph of FIG. 4B. At this stage, more than one candidate for cross-sectional shape of the specimen 7 can be obtained by changing values of the parameters n and k.

Figure 5:
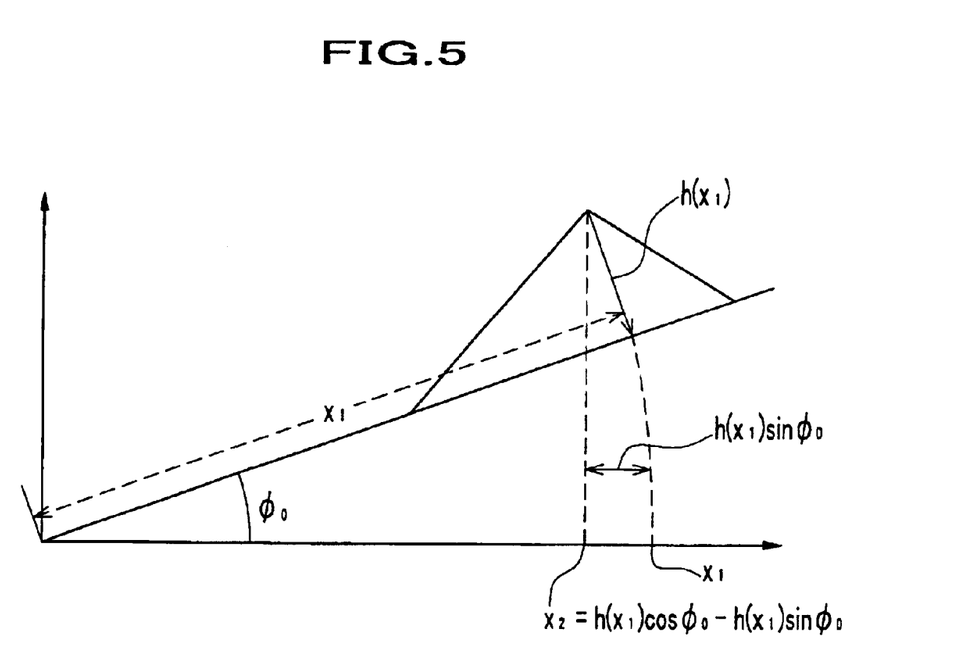
FIG. 5 is a graph showing a principle of stereoscopy based upon a tilt of a stage on which a specimen is placed.

Next, a simulation for the candidates for cross-sectional shape of the specimen 7 determined using Equation (3) is performed to estimate signal intensities of electron beams generated from the candidates for cross-sectional shape of the specimen 7 to be obtained if each electron beam is applied with the tilt angle $\phi$ changed from $\phi=0$ to $\phi=\phi_0$ as shown in FIG. 5 (step 206). At this stage, a point on the specimen 7 observed at a position $x_1$ before the specimen 7 is tilted and is observed at a position $x_2$ after the specimen 7 is tilted. For example, assuming that the cross section profile h(x) is expressed in a triangle, a position of the vertex of the triangle can be observed at a position $x_1$ before the specimen 7 is tilted and is observed at a position $x_2$ after the specimen 7 is tilted at a tilt angle $\phi=\phi_0$. If the signal intensity obtained with the tilt angle $\phi=\phi_0$ is $I_{S1}(x)$ and the signal intensity obtained after the specimen is tilted with the tilt angle $\phi=\phi_0$ is $I_{S2}(x)$, the above phenomenon is expressed in $I_{S1}(x_1)+\delta I(x_1)=I_{S2}(x_2)$ where $x_1$ and $x_2$ are distances from the rotation center 0 of the stage 2 (positions on an axis parallel to the scanning direction), $\delta I(x_1)$ is an increment/decrement of $I_{S1}(x)$ caused by the condition as shown in Equation (1) when the specimen having a cross-sectional shape obtained by Equation (3) is tilted at the tilt angle $\phi=\phi_0$. The value of $\delta I(x_1)$ is obtained using Equation (4) derived from Equation (1) as follows:

$$\delta I(x_1) = kI(\sec^n(\theta(x_1)+\phi_0) - \sec^n \theta(x_1)) \quad (4)$$

x2 is expressed by Equation (5) below as apparent from FIG. 5:

$$x_2 = x_1 \cos \phi_0 - h(x_1) \sin \phi_0 \quad (5)$$

Accordingly, substituting Equation (5) into the equation $I_{S1}(x_1)+\delta I(x_1)=I_{S2}(x_2)$ yields Equation (6) as follows:

$$I_{S1}(x_1) + \delta I(x_1) = I_{S2}(x_1 \cos \phi_0 - h(x_1) \sin \phi_0) \quad (6)$$

Equation (6) represents simulation of determination, utilizing $I_{S1}(x)$, of $I_{S2}(x)$ to be obtained after the specimen 7 is tilted. In Equation (6), if an estimated candidate for cross-sectional shape indicates an adequate cross-sectional shape of the specimen 7, it is assumed that brightness is not changed before and after the specimen 7 is tilted.

Next, each $I_{S2}$ is compared with the left-hand side of Equation (6), to determine whether a difference therebetween is the minimum.

In this instance, the bounds of scanning (distance in the scanning direction) 0–1 are compared utilizing Equation (7) as follows:

$$E = \int_0^1 \{I_{S1}(x) + \delta I(x) - I_{S2}(x\cos\phi_0 - h(x)\sin\phi_0)\}^2 dx \quad (7)$$

It is to be noted that an error in tilting operation of the specimen 7 could possibly cause a deviation in the origin of the coordinate between that used for measuring $I_{S1}(x)$ before the tilting operation and that used for measuring $I_{S2}(X)$ after the tilting operation. Accordingly, a parameter $\Delta x$ for compensating the deviation is added as another three-dimensional shape parameter.

Further, when comparison is made according to Equation (7), a value E at each scanning position is plotted in sequence according to Equation (7), to determine whether the value E is the minimum value. If it is determined that the value E is not the minimum value, each value of the parameters n and k is changed and the process in steps 205 through 208 are repeatedly performed. The same process is repeated until it is determined that the value E becomes the minimum value, and if it is determined that the minimum value for one scan line is acquired, then an absolute value of the height (distance along z-axis) is obtained as a cross-sectional shape (two-dimensional shape) of the specimen 7 for the scan line. Subsequently, after the cross-sectional shape of the specimen 7 is thus determined for that one scan line, a value E for each of the other multiple scan lines is accumulated each time when the scan line is shifted in a direction parallel to the y-axis. Based upon the accumulated values E (cross-sectional shapes of the specimen 7) for the scan lines, the three-dimensional shape of the specimen 7 is determined, and the determination result is output (step 210).

Figure 6A:
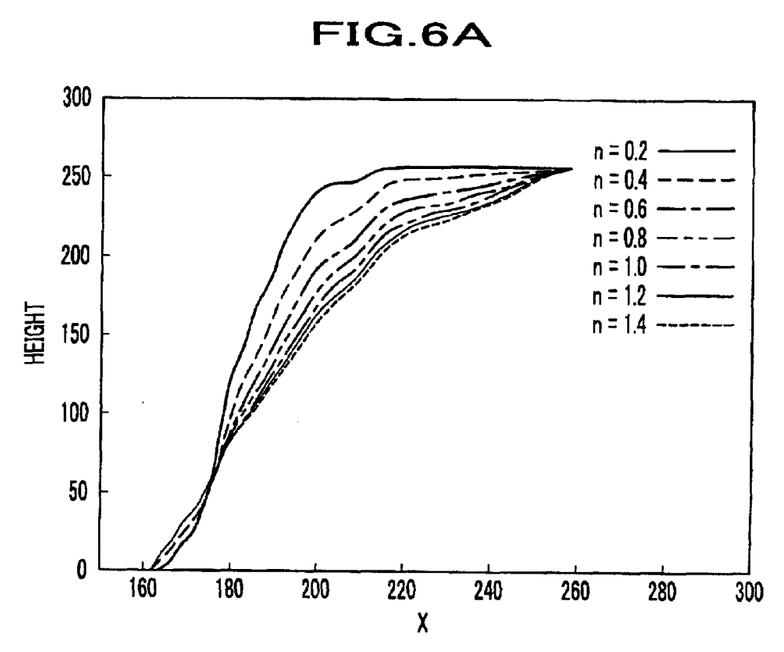
FIG. 6A is a graph showing cross-sectional shape candidates of a specimen determined by changing a parameter n.
Figure 6B:
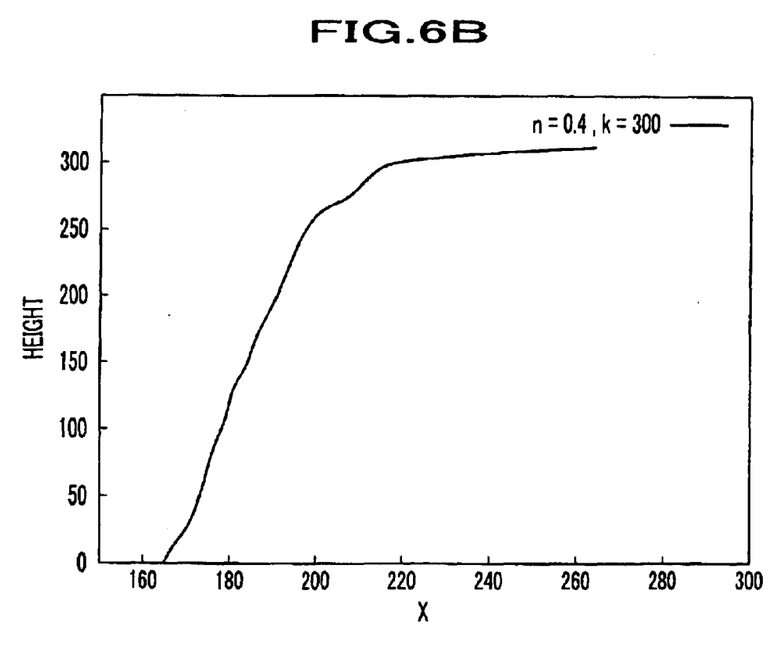
FIG. 6B is a graph showing a resultant cross-sectional shape of a specimen finally determined by changing parameters n and k.

An exemplified set of multiple candidates for cross-sectional shape determined by varying the parameter n only is depicted in FIG. 6A. In actuality, there also exist candidates for cross-sectional shape determined by varying the parameters k, $\Delta x$. Therefore, the most appropriate parameters are determined among these multiple candidates for cross-sectional shape, by repeating the process in steps 205 through 209. An exemplified cross-sectional shape obtained with the optimum combination of the parameters determined by varying the parameters in sequence is depicted in FIG. 6B.

A database is constructed in which parameters n, k, and $\Delta x$ determined by repeatedly performing the steps 205 through 209, and candidates for cross-sectional shape, comparison errors in signal waveforms, and an actual cross-sectional shape (if available) corresponding to each combination of the parameters are stored. As a result, Equations (2) and (3) for defining a scheme used in the "Shape from shadings" method in step 205, and parameters determined in step 204 can be reviewed for appropriateness, by analyzing the database. In addition, once it is determined that the above equations and parameters are appropriate, a cross-sectional shape for an input signal in step 203 can directly be determined by consulting the database without performing calculations in the "Shape from shading" method.

Although the preferred embodiments of the present invention have been described above, various modifications and changes may be made in the present invention without departing from the spirit and scope thereof.

For example, in the embodiment as described above, an angle of an electron beam incident on the surface of a specimen 7 is changed by changing the tilt angle of the stage 2; however, any other techniques for changing the angle of incidence of the electron beam may be adopted: such as biasing of the electron beam, and insertion of material having a specific known slope angle between the specimen 7 and the stage 2. Such alternative techniques can serve to implement the same process without a mechanism for changing a tilt angle of the stage 2.

Furthermore, an electron beam is used by way of example as charged particles to be applied to the specimen 7, in the present embodiment, but protons may be used instead of charged particles; thus, an electromagnetic wave such as a visible ray, an ultraviolet ray, etc. can be employed as well. In cases where such an electromagnetic wave is employed, an electromagnetic wave is applied to the specimen 7, and a signal intensity of the electromagnetic wave reflected from the specimen 7 is to be measured.

As described above, the preferred embodiments of the present invention make use of simulation of input signal waveforms, and thus require no process for matching feature points of a stereoscopic image to acquire an absolute value of the height of the cross sectional shape of the specimen 7. Moreover, as distinct from the Spectroscopic Critical Dimension Metrology, three-dimensional shapes of varied patterns can be measured with ease.

According to the present invention, a cross-sectional shape of a specimen can be obtained utilizing an absolute value of the height of the specimen without utilizing a matching process of feature points. Further, the cross-sectional shapes obtained by irradiation with an electromagnetic wave or a beam of charged particles along an axis parallel to the scanning direction is accumulated and stored each time when the irradiation unit moves along an axis perpendicular to the scanning direction, so that a three-dimensional shape of the specimen can be obtained.

What is claimed is:

1. A shape measurement method comprising the steps of:
    applying one of an electromagnetic wave and a beam of charged particles to a surface of a specimen, using an irradiation unit that moves along an axis parallel to a scanning direction relative to the surface of the specimen;
    measuring a signal intensity of one of an electromagnetic wave reflected from the surface of the specimen and a beam of charged particles generated from the surface of the specimen as a result of irradiation from the irradiation unit;
    calculating a slope angle of the surface of the specimen at a position irradiated with one of the electromagnetic wave and the beam of charged particles on the basis of the measured signal intensity;
    determining candidates for cross-sectional shape of the specimen on the basis of the calculated slope angle;
    estimating a signal intensity of one of an electromagnetic wave that would be reflected from a surface having a cross-sectional shape of each of the candidates and a beam of charged particles that would be generated from the surface having a cross-sectional shape of each of the candidates if an angle of incidence of one of the electromagnetic wave and the beam of charged particles with respect to the surface having a cross-sectional shape of each of the candidates were changed to a specific angle of incidence different from an angle of incidence of one of the electromagnetic wave and the beam of charged particles applied to the surface of the specimen;
    comparing the estimated signal intensity with a signal intensity obtained by measurement performed when the angle of incidence of one of the electromagnetic wave and the beam of charged particles applied to the surface of the specimen is changed to the specific angle of incidence; and
    determining the cross-sectional shape of the specimen on the basis of a result of the comparing step.

2. A shape measurement method according to claim 1, in which the irradiation unit further moves along an axis perpendicular to the scanning direction relative to the surface of the specimen, the shape measurement method further comprising the steps of:
    accumulating the determined cross-sectional shape each time when the irradiation unit moves along the axis perpendicular to the scanning direction; and
    determining a three-dimensional shape of the specimen on the basis of a result of the accumulating step.

3. A shape measurement method according to claim 1, wherein the step of calculating the slope angle of the surface of the specimen at a position irradiated with one of the electromagnetic wave and the beam of charged particles is performed using the measured signal intensity and multiple parameters selected from various kinds of parameters relating to the cross-sectional shape of the specimen.

4. A shape measurement method according to claim 3, wherein the multiple parameters to be used are selected among those serving to reduce a difference between the measured signal intensity and the estimated signal intensity.

5. A shape measurement method according to claim 3, wherein the multiple parameters are repeatedly selected until a difference between the measured signal intensity and the estimated signal intensity is reduced to a minimum.

6. A shape measurement method according to claim 3, wherein the candidates for cross-sectional shape that have been determined, the cross-sectional shape that has been determined, and the multiple parameters that have been selected are stored in a database.

7. A shape measurement method according to claim 1, wherein when the angle of incidence of one of the electromagnetic wave and the beam of charged particles applied to the surface of the specimen is changed to the specific angle of incidence, one of an angle of placement of the specimen and an angle of irradiation of the irradiation unit is changed while the other of the angle of placement of the specimen and the angle of irradiation of the irradiation unit is fixed at a predetermined angle.

8. A shape measurement apparatus comprising:
    an irradiation unit that applies one of an electromagnetic wave and a beam of charged particles to a surface of a specimen, while moving along an axis parallel to a scanning direction relative to the surface of the specimen;
    a signal intensity measurement unit that measures a signal intensity of one of the electromagnetic wave reflected from the surface of the specimen and the beam of charged particles generated from the surface of the specimen as a result of irradiation from the irradiation unit;
    a cross-sectional shape candidate determination unit that calculates a slope angle of the surface of the specimen at a position irradiated with one of the electromagnetic wave and the beam of charged particles on the basis of the signal intensity measured in the signal intensity measurement unit, and determines candidates for cross-sectional shape of the specimen on the basis of the calculated slope angle;
    a signal intensity estimation unit that estimates a signal intensity of one of an electromagnetic wave that would be reflected from a surface having a cross-sectional shape of each of the candidates and a beam of charged particles that would be generated from the surface having a cross-sectional shape of each of the candidates if an angle of incidence of one of the electromagnetic wave and the beam of charged particles with respect to the surface having a cross-sectional shape of each of the candidates were changed to a specific angle of incidence different from an angle of incidence of one of the electromagnetic wave and the beam of charged particles applied to the surface of the specimen; and
    a cross-sectional shape determination unit that compares the signal intensity estimated in the signal intensity estimation unit with a signal intensity obtained by measurement performed in the signal intensity measurement unit when the angle of incidence of one of the electromagnetic wave and the beam of charged particles applied to the surface of the specimen is changed to the specific angle of incidence, and determines the cross-sectional shape of the specimen on the basis of a result of the comparison.

9. A shape measurement apparatus according to claim 8, wherein the irradiation unit further moves along an axis perpendicular to the scanning direction relative to the surface of the specimen; and wherein the cross-sectional shape determination unit accumulates the determined cross-sectional shape each time when the irradiation unit moves along the axis perpendicular to the scanning direction, and determines a three-dimensional shape of the specimen on the basis of the accumulated cross-sectional shapes.

10. A shape measurement apparatus according to claim 8, wherein the cross-sectional shape candidate determination unit uses the signal intensity measured in the signal intensity measurement unit and multiple parameters selected from various kinds of parameters relating to the cross-sectional shape of the specimen to calculate the slope angle of the surface of the specimen at a position irradiated with one of the electromagnetic wave and the beam of charged particles.

11. A shape measurement apparatus according to claim 10, wherein the cross-sectional shape determination unit instructs the cross-sectional shape candidate determination unit to select the multiple parameters among those serving to reduce a difference between the signal intensity measured in the signal intensity measurement unit and the signal intensity estimated in the signal intensity estimation unit.

12. A shape measurement apparatus according to claim 10, wherein the cross-sectional shape determination unit instructs the cross-sectional shape candidate determination unit to repeatedly select the multiple parameters until a difference between the signal intensity measured in the signal intensity measurement unit and the signal intensity estimated in the signal intensity estimation unit is reduced to a minimum.

13. A shape measurement apparatus according to claim 10, wherein the candidates for cross-sectional shape that have been determined in the cross-sectional shape candidate determination unit, the cross-sectional shape that has been determined in the cross-sectional shape determination unit, and the multiple parameters that have been selected in the cross-sectional shape candidate determination unit are stored in a database.

* * * * *